US006391594B1

(12) United States Patent
Khosla et al.

(10) Patent No.: US 6,391,594 B1
(45) Date of Patent: May 21, 2002

(54) MODIFIED MODULAR PKS WITH RETAINED SCAFFOLD

(75) Inventors: Chaitan Khosla, Stanford; Gary Ashley, Alameda; Hong Fu; Camilla M. Kao, both of Stanford; Robert McDaniel, Palo Alto, all of CA (US)

(73) Assignees: Kosan Biosciences, Inc., Hayward; The Leland Stanford Junior University, Palo Alto, both of CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/846,247

(22) Filed: Apr. 30, 1997

Related U.S. Application Data

(63) Continuation-in-part of application No. 08/846,645, filed on Jun. 7, 1995, now Pat. No. 5,712,146, which is a continuation-in-part of application No. 08/238,811, filed on May 6, 1994, now Pat. No. 5,672,491, which is a continuation-in-part of application No. 08/164,301, filed on Dec. 8, 1993, now abandoned, which is a continuation-in-part of application No. 08/123,732, filed on Sep. 20, 1993, now abandoned.

(51) Int. Cl.[7] .......................... C12N 15/64; C12N 9/00; C12N 1/20; C07H 21/04

(52) U.S. Cl. ...................... 435/91.4; 435/183; 435/193; 435/455; 435/471; 435/486; 435/252.35; 435/320.1; 536/23.2

(58) Field of Search .................................. 435/183, 435, 435/91.4, 76, 252.35, 320.1, 455, 471, 193, 486; 536/23.2

(56) References Cited

U.S. PATENT DOCUMENTS

| | | | |
|---|---|---|---|
| 5,168,052 A | 12/1992 | Cox et al. | 435/72 |
| 5,672,491 A | * 9/1997 | Khosla et al. | 435/148 |
| 5,824,513 A | 10/1998 | Katz et al. | 435/76 |
| 5,876,991 A | 3/1999 | DeHoff et al. | 435/183 |
| 5,945,320 A | 8/1999 | Burgett et al. | 435/183 |
| 6,004,787 A | 12/1999 | Katz et al. | 435/183 |
| 6,200,813 B1 | 3/2001 | Katz et al. | 435/477 |
| 6,271,255 B1 | 8/2001 | Leadlay et al. | 514/450 |

FOREIGN PATENT DOCUMENTS

| | | |
|---|---|---|
| WO | WO 93/13663 | 7/1993 |
| WO | 96/40968 | 12/1996 |
| WO | WO 98/01546 | 1/1998 |
| WO | 98/01546 | 1/1998 |
| WO | 98/01571 | 1/1998 |
| WO | WO 98/51695 | 11/1998 |

OTHER PUBLICATIONS

Tsoi, C.J., et al., "Combinatorial Biosynthesis of 'Unnatural' Natural Products: the Polyketide Example," *Chemistry & Biology*, (Jun. 1985) 2:355–362.

Donadio, Stefano, et al., "An Erythromycin Analog Produced by Reprogramming of Polyketide Synthesis," *Proc. Natl. Acad. Sci. USA*, vol. 90, pp. 7119–7123.

Sherman, David H., et al., "Functional Replacement of Genes for Individual Polyketide Synthase Components in *Streptomyces coelicolor* A3(2) by Heterologous Genes from a Different Polyketide Pathway," *Journal of Bacteriology*, (Oct. 1992), pp. 6184–6190.

Brown et al., "A Mutant Generated by Expression of an Engineered DEBS1 Protein from the Erythromycin–Producing Polyketide Synthase (PKS) in Streptomyces Coelicolor Produces the Triketide as a Lactone, but the Major Product is the Nor–Analogue Derived from Acetate as Starter Acid," J Chem Soc Chem Commun (1995) 15:1517–1518.

Khosla, Chaitan et al., "Generation of polyketide libraries via combinatorial biosynthesis," Tibtech Sep. 1996 (vol. 14) pp. 335–341.

Kao, Camilla M. et al., "Engineered Biosynthesis of a Complete Macrolactone in a Heterologous Host," Science (vol. 265) Jul. 22, 1994, pp. 509–512.

Oliynyk, M. et al., *Chem and Biol* (1996), 3:833–839.

Kuhstoss, S. et al., *Gene* (1996) 183:231–236.

Bartel et al. (1990) "Biosynthesis of anthraquinones by interspecies cloning of actinorhodin biosynthesis genes in streptomycetes: Clarification of actinorhodin gene functions," *J. Bacteriol.* 172(9):4816–4826.

Beck et al. (1990) "The multifunctional 6–methylsalicyclic acid synthase gene of *Penicillium patulum*. Its gene structure relative to that of other polyketide synthases," *Eur. J. Biochem* 192:487–498.

Bibb et al. (1989) "Analysis of the nucleotide sequence of the streptomyces glaucescens tcml genes provided key information about the enzymology of polyketide antibiotic biosynthesis," *EMBO J.* 8(9):2727–2736.

Caballero et al. (1991) "Organisation and functions of the actVA region of the actinorhodin biosynthetic gene cluster of *Streptomyces coelicolor*," *Mol. Gen. Genet.* 230:401–412.

Cortes et al. (1990) "An unusually large multifunctional polypeptide in the erythromycin–producing polyketide synthase.of *Saccharopolyspora erythraea*," *Nature* (1990) 348:176–178.

Donadio et al. (1991) "Modular organization of genes required for complex polyketide biosynthesis," *Science* 252:675–679.

(List continued on next page.)

Primary Examiner—Nashaat T. Nashed
(74) Attorney, Agent, or Firm—Morrison & Foerster LLP

(57) ABSTRACT

Combinatorial libraries of polyketides can be obtained by suitable manipulation of a host modular polyketide synthase gene cluster such as that which encodes the PKS for erythromycin. The combinatorial library is useful as a source of pharmaceutically active compounds.

16 Claims, 8 Drawing Sheets

OTHER PUBLICATIONS

Donadio et al. (1992) "Biosynthesis of the erythromycin macrolactone and a rational approach for producing hybrid macrolides," *Gene* 115:97–103.

Fernandez–Moreno et al. (1991) "The act cluster contains regulatory and antibiotic export genes, direct targets for translational control by the bldA tRNA gene of Streptomyces," *Cell* 66:769–780.

Fernandez–Moreno et al. (1992) "Nucleotide sequence and deduced functions of a set of cotranscribed genes of *Streptomyces coelicolor* A3(2) including the polyketide synthase for the antibiotic actinorhodin," *J. Biol. Chem.* 267:19278–19290.

Floss (1991) "Genetic engineering of hybrid antibiotics—a progress report," *Tetrahydron* 47(31):6045–6058.

Fu (1994) "Engineered biosynthesis of novel polyketides: Stereochemical course of two reactions catalyzed by a polyketide synthase," *Biochemistry* 33(31):9321–9326.

Hallam (1988) "Nucleotide sequence, transcription and deduced function of a gene involved in polyketide antibiotic synthesis in *Streptomyces coelicolor*," *Gene* 74:305–320.

Hopwood et al. (1985) "Product of 'hybrid' antibiotics by genetic engineering," *Nature* 314 (6012):642–644.

Katz et al. (1993) "Polyketide synthesis: Prospects for hybrid antibiotics," *Ann. Review Microbiol.* 47:875–912.

Khosla et al. (1993) "Genetic construction and functional analysis of hybrid polyketide synthases containing heterologous acyl carrier proteins," *J. Bacteriol.* 175:2197–2204.

Khosla et al. (1992) "Targeted gene replacements in a Streptomyces polyketide synthase gene cluster: role for the acyl carrier protein," *Molec. Microbiol.* 6(21):3237–3249.

MacNeil et al. (1992) "Complex organization of the *Streptomyces avermitilis* genes encoding the avermectin polyketide synthase," *Gene* 115:119–125).

Malpartida et al. (1984) "Molecular cloning of the whole biosynthetic pathway of a streptomyces antibiotic and its expression in a heterologous host," *Nature* 309:462–464.

Malpartida et al. (1986) "Physical and genetic characterisation of the gene cluster for the antibiotic actinorhodin in *Streptomyces coelicolor* A3(2)," *Mol. Gen. Genet.* 205:66–73.

Malpartida et al. (1987) "Homology between streptomyces genes coding for synthesis of different polyketides used to clone antibiotic biosynthetic genes," *Nature* 325(6107):818–821.

McDaniel et al. (1993) Engineered biosynthesis of novel polyketides, *Science* 262:1546–1550.

Sherman et al. (1992) "Functional replacement of genes for individual polyketide synthase components in *Streptomyces coelicolor* A3(2) by hetergenous genes from a different polyketide pathway," *J. Bacteriol.* 174:6184–6190.

Sherman et al. (1989) "Structure and deduced function of the granaticin–producing polyketide synthase gene cluster of *Streptomyces violaceoruber* Tü22," *EMBO J.* 8:2717–2725.

Perun, T.J., Drug Action and Drug Resistance in Bacteria, vol. 1, S. Mitsuhashi (ed) Univ. Park Press, Baltimore, 1977.

Donadio et al., Industrial Microorganism, Basic and Applied Molecular Genetics (1993), R.H. Baltz, G.D. Hegeman and P1L. Skatrud (eds) (Amer. Soc. Microbial), Washington, DC. pp. 257–265.

* cited by examiner 11-19A 11-21A 11-22A 11-25A: R=Et
11-25B: R=Me

CK7A: R=Me
CK7B: R=H

MODIFIED MODULAR PKS WITH RETAINED SCAFFOLD

CROSS-REFERENCE TO RELATED APPLICATIONS

This Application is a continuation-in-part of U.S. Ser. No. 08/486,645, filed Jun. 7, 1995 and now U.S. Pat. No. 5,712,146, issued on Jan. 27, 1998, which is continuation-in-part of U.S. Ser. No. 08/238,811, filed May 6, 1994 and now U.S. Pat. No. 5,672,491, issued on Sep. 30, 1997 which is a continuation-in-part of U.S. Ser. No. 08/164,301, filed Dec. 8, 1993 and now abandoned, which is a continuation-in-part of U.S. Ser. No. 08/123,732, filed Sep. 20, 1993 and now abandoned. The disclosures of these applications are incorporated herein by reference.

REFERENCE TO GOVERNMENT FUNDING

This work was supported in part by a grant from the National Institutes of Health, CA66736. The U.S. government has certain rights in this invention.

TECHNICAL FIELD

The invention relates to the field of combinatorial libraries. More particularly, it concerns construction of libraries of polyketides synthesized by a multiplicity of polyketide synthases derived from a naturally occurring PKS, as illustrated by the erythromycin gene cluster.

BACKGROUND ART

Polyketides represent a large family of diverse compounds ultimately synthesized from 2-carbon units through a series of Claisen-type condensations and subsequent modifications. Members of this group include antibiotics such as tetracyclines, anticancer agents such as daunomycin, and immunosuppressants such as FK506 and rapamycin. Polyketides occur in many types of organisms including fungi and mycelial bacteria, in particular, the actinomycetes.

The polyketides are synthesized by polyketide synthases (PKS). This group of enzymatically active proteins is considered in a different category from the fatty acid synthases which also catalyze condensation of 2-carbon units to result in, for example, fatty acids and prostaglandins. Two major types of PKS are known which are vastly different in their construction and mode of synthesis. These are commonly referred to as Type I or "modular" and Type II, "aromatic."

The PKS scaffold that is the subject of the present invention is a member of the group designated Type I or "modular" PKS. In this type, a set of separate active sites exists for each step of carbon chain assembly and modification, but the individual proteins contain a multiplicity of such separate active sites. There may be only one multifunctional protein of this type, such as that required for the biosynthesis of 6-methyl salicylic acid (Beck, J. et al., *Eur J Biochem* (1990) 192:487–498; Davis, R. et al., *Abstracts of Genetics of Industrial Microorganism Meeting,* Montreal, Abstract P288 (1994)). More commonly, and in bacterial-derived Type I PKS assemblies, there are several such multifunctional proteins assembled to result in the end product polyketide. (Cortes, J. et al., *Nature* (1990) 348:176; Donadlo, S. et al., *Science* (1991) 1S2:673; MacNeil, D. J. et al., *Gene* (1992) 115:119.)

The PKS for erythromycin, used as an illustrative system is a modular PKS. Erythromycin was originally isolated from *S. erythraeus* (since reclassified as *Saccharopolyspora erythraea*) which was found in a soil sample from the Philippine archipelago. Cloning the genes was described by Donadio, S. et al., *Science* (1991) 252:675. The particulars have been reviewed by Perun, T. J. in *Drug Action and Drug MResistance in Bacteria,* Vol. 1, S. Mitsuhashi (ed.) University Park Press, Baltimore, 1977. The antibiotic occurs in various glycosylated forms, designated A, B, C, and D during various stages of fermentation. The entire erythromycin biosynthetic gene cluster from *S. erythraeus* has been mapped and sequenced by Donadio et al. in *Industrial Microorganisms: Basic and Applied Molecular Genetics* (1993) R. H. Baltz, G. D. Hegeman, and P. L. Skatrud (eds.) (*Amer Soc Microbiol*) and the entire PKS is an assembly of three such multifunctional proteins usually designated DEBS-1, DEBS-2, and DEBS-3, encoded by three separate genes.

Type II PKS, in contrast, include several proteins, each of which is simpler than those found in Type I polyketide synthases. The active sites in these enzymes are used iteratively so that the proteins themselves are generally monofunctional or bifunctional. For example, the aromatic PKS complexes derived from Streptomyces have so far been found to contain three proteins encoded in three open reading frames. One protein provides ketosynthase (KS) and acyltransferase (AT) activities, a second provides a chain length determining factor (CLDF) and a third is an acyl carrier protein (ACP).

The present invention is concerned with PKS systems derived from modular PKS gene clusters. The nature of these clusters and their manipulation are further described below.

DISCLOSURE OF THE INVENTION

The invention provides recombinant materials for the production of combinatorial libraries of polyketides wherein the polyketide members of the library are synthesized by various PKS systems derived from naturally occurring PKS systems by using these systems as scaffolds. Generally, many members of these libraries may themselves be novel compounds, and the invention further includes novel polyketide members of these libraries. The invention also includes methods to recover novel polyketides with desired binding activities by screens the libraries of the invention.

Thus, in one aspect, the invention is directed to a multiplicity of cell colonies comprising a library of colonies wherein each colony of the library contains an expression vector for the production of a different modular PKS, but derived from a naturally occurring PKS. In a preferred embodiment, the different PKS are derived from the erythromycin PKS. In any case, the library of different modular PKS is obtained by modifying one or more of the regions of a naturally occurring gene or gene cluster encoding an enzymatic activity so as to alter that activity, leaving intact the scaffold portions of the naturally occurring gene. In another aspect, the invention is directed to a multiplicity of cell colonies comprising a library of colonies wherein each colony of the library contains a different modular PKS derived from a naturally occurring PKS, preferably the erythromycin PKS. The invention is also directed to methods to produce libraries of PKS complexes and to produce libraries of polyketides by culturing these colonies, as well as to the libraries so produced. In addition, the invention is directed to methods to screen the resulting polyketide libraries and to novel polyketides contained therein.

MODES OF CARRYING OUT THE INVENTION

It may be helpful to review the nature of the erythromycin PKS complex and the gene cluster that encodes it as a model for modular PKS, in general.

Figure 1:
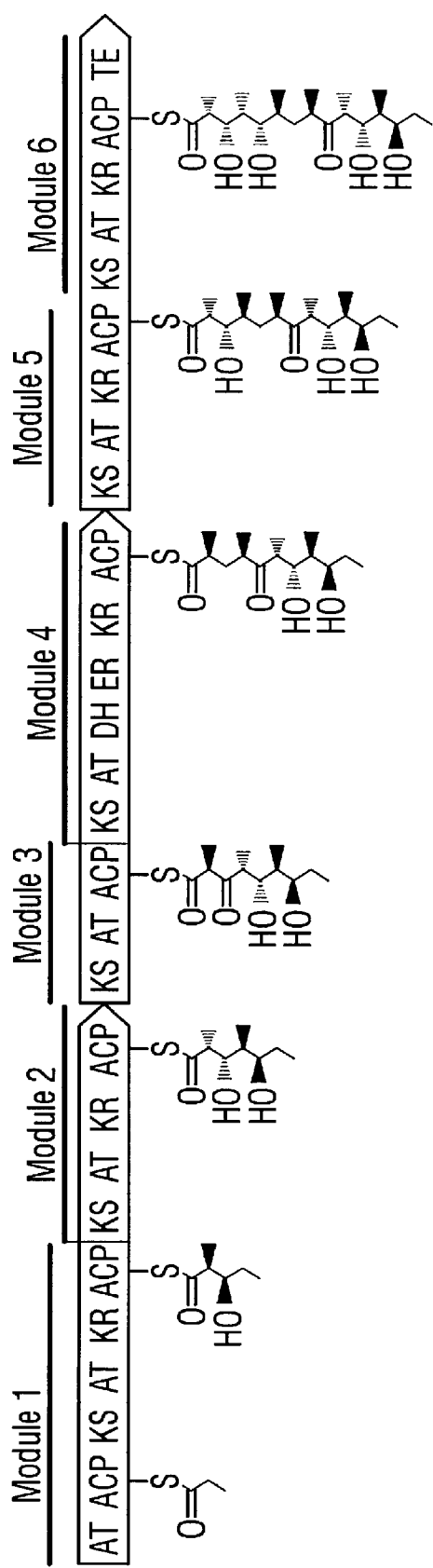
FIG. 1 is a diagram of the erythromycin PKS complex from *S. erythraeus* showing the function of each multifunctional protein.

FIG. 1 is a diagrammatic representation of the gene cluster encoding erythromycin. The erythromycin PKS protein assembly contains three high-molecular-weight proteins (>200 kD) designated DEBS-1, DEBS-2 and DEBS-3, each encoded by a separate gene (Caffrey et al., *FEBS Lett* (1992) 304:225). The diagram in FIG. 1 shows that each of the three proteins contains two modules of the synthase—a module being that subset of reactivities required to provide an additional 2-carbon unit to the molecule. As shown in FIG. 1, modules 1 and 2 reside on DEBS-1; modules 3 and 4 on DEBS-2 and modules 5 and 6 on DEBS-3. The minimal module is typified in module 3 which contains a ketosynthase (KS), an acyltransferase (AT) and an acyl carrier protein (ACP). These three functions are sufficient to activate an extender unit and attach it to the remainder of the growing molecule. Additional activities that may be included in a module relate to reactions other than the Claisen condensation, and include a dehydratase activity (DH), an enoylreductase activity (ER) and a ketoreductase activity (KR). The first module also contains repeats of the AT and ACP activities because it catalyzes the initial condensation, i.e. it begins with a "loading domain" represented by AT and ACP, which determine the nature of the starter unit. Although not shown, module 3 has a KR region which therefore is inactive. The "finishing" of the molecule is regulated by the thioesterase activity (TE) in module 6. This thioesterase appears to catalyze cyclization of the macrolide ring thereby increasing the yield of the polyketide product.

Figure 2:
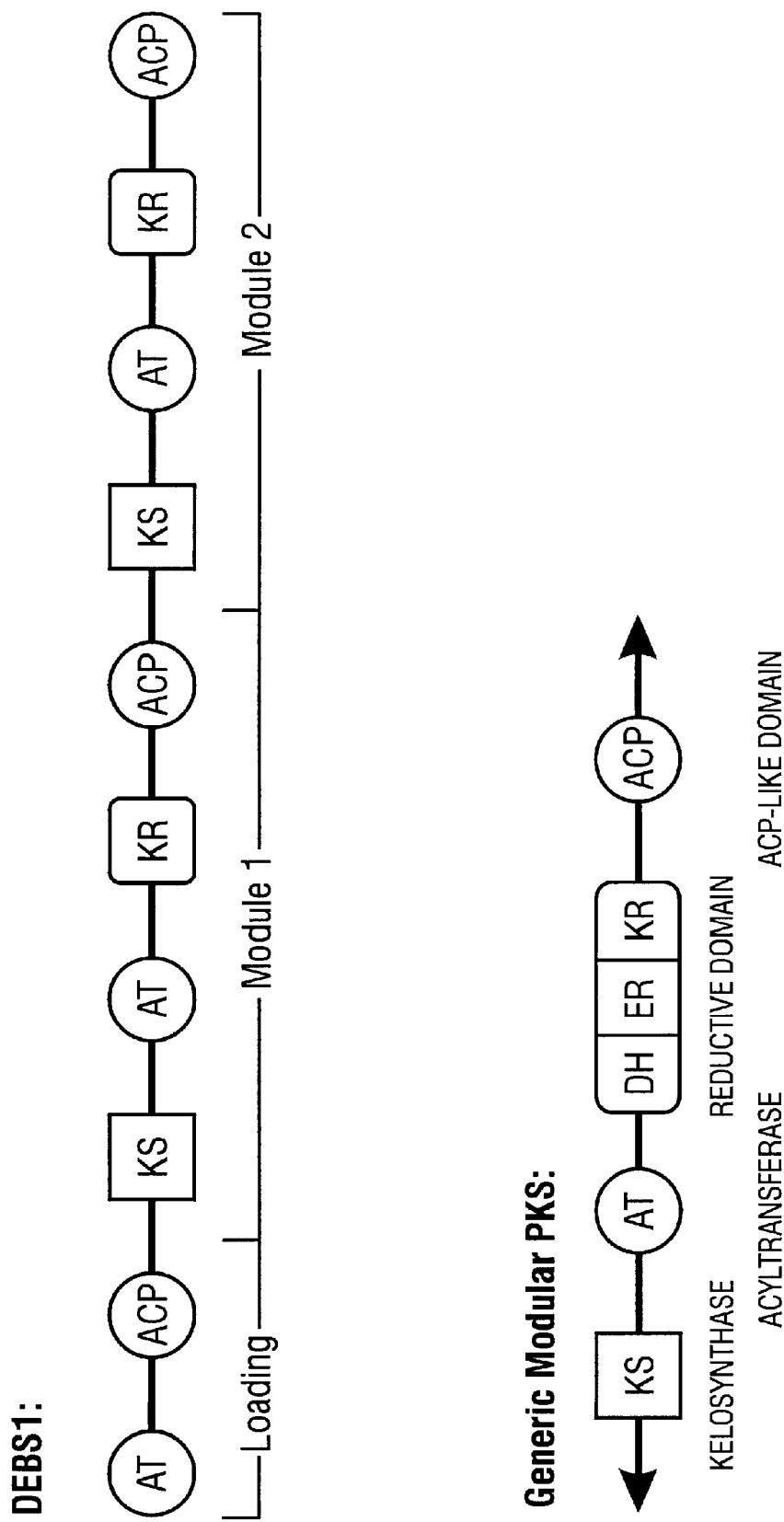
FIG. 2 is a diagram of DEBS-1 from *S. erythraeus* showing the functional regions separated by linker regions.

FIG. 2 shows a detailed view of the regions in the first two modules which comprise the first open reading frame encoding DEBS-1. The regions that encode enzymatic activities are separated by linker or "scaffold"-encoding regions. These scaffold regions encode amino acid sequences that space the enzymatic activities at the appropriate distances and in the correct order. Thus, these linker regions collectively can be considered to encode a scaffold into which the various activities are placed in a particular order and spatial arrangement. This organization is similar in the remaining genes, as well as in other naturally occurring modular PKS gene clusters.

The three DEBS-1, 2 and 3 proteins are encoded by the genetic segments erYAI, eryAII, and eryAIII, respectively. These reading frames are located on the bacterial chromosome starting at about 10 kb distant from the erythromycin resistance gene (ermE or eryR).

The detailed description above referring to erythromycin is typical for modular PKS in general. Thus, rather than the illustrated erythromycin, the polyketide synthases making up the libraries of the invention can be derived from the synthases of other modular PKS, such as those which result in the production of rapamycin, avermectin, FK-506, FR-008, monensin, rifamycin, soraphen-A, spinocyn, squalestatin, or tylosin, and the like.

Regardless of the naturally occurring PKS gene used as a scaffold, the invention provides libraries, ultimately of polyketides, by generating a variety of modifications in the erythromycin PKS or other naturally occurring PKS gene cluster so that the protein complexes produced by the cluster have altered activities in one or more respects, and thus produce polyketides other than the natural product of the PKS. By providing a large number of different genes or gene clusters derived from a naturally occurring PKS gene cluster, each of which has been modified in a different way from the native cluster, an effectively combinatorial library of polyketides can be produced as a result of the multiple variations in these activities. All of the PKS encoding sequences used in the present invention represent modular polyketide synthases "derived from" a naturally occurring PKS, illustrated by the erythromycin PKS. As will be further described below, the metes and bounds of this derivation can be described on both the protein level and the encoding nucleotide sequence level.

By a modular PKS "derived from" the erythromycin or other naturally occurring PKS is meant a modular polyketide synthase (or its corresponding encoding gene(s)) that retains the scaffolding of all of the utilized portion of the naturally occurring gene. all modules need be included in the constructs.) On the constant scaffold, at least one enzymatic activity is mutated, deleted or replaced, so as to alter the activity. Alteration results when these activities are deleted or are replaced by a different version of the activity, or simply mutated in such a way that a polyketide other than the natural product results from these collective activities. This occurs because there has been a resulting alteration of the starter unit and/or extender unit, and/or stereochemistry, and/or chain length or cyclization and/or reductive or dehydration cycle outcome at a corresponding position in the product polyketide. Where a deleted activity is replaced, the origin of the replacement activity may come from a corresponding activity in a different naturally occurring polyketide synthase or from a different region of the same PKS. In the case of erythromycin, for example, any or all of the DEBS-1, DEBS-2 and DEBS-3 proteins may be included in the derivative or portions of any of these may be included; but the scaffolding of an erythromycin PKS protein is retained in whatever derivative is considered. Similar comments pertain to the corresponding ery-AI, ery-AII and ery-AIII genes.

The derivative may contain preferably at least a thioesterase activity from the erythromycin or other naturally occurring PKS gene cluster.

In summary, a polyketide synthase "derived from" a naturally occurring PKS contains the scaffolding encoded by all or the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized.

Thus, there are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, or ethyl malonyl, etc. Third, the loading domain specificity will also have an effect on the resulting carbon skeleton of the polyketide. Thus, the loading domain may use a different starter unit, such as acetyl, propionyl, and the like. Fourth, the oxidation state at various positions of the polyketide will be determined by the dehydratase and reductase portions of the modules. This will determine the presence and location of ketone, alcohol, alkene substituents or whether a single σ-bond will result at particular locations in the polyketide. Finally, the stereochemistry of the resulting polyketide is a function of three aspects of the synthase. The first aspect is related to the AT/KS specificity associated with substituted malonyls as extender units, which affects stereochemitry only when the reductive cycle is missing or when it contains only a ketoreductase since the dehydratase would abolish chirality. Second, the specificity of the ketoreductase will determine the chirality of any β-OH. Finally, the enoyl reductase specificity for substituted malonyls as extender units will influence the result when there is a complete KR/DH/ER available.

In the working examples below, all of the foregoing variables other than the loading domain specificity which controls the starter unit have been varied.

Thus, the modular PKS systems, and in particular, the erythromycin PKS system, permit a wide range of polyketides to be synthesized. As compared to the aromatic PKS systems, a wider range of starter units including aliphatic monomers (acetyl, propionyl, butyryl, isovaleryl, etc.), aromatics (aminohydroxybenzoyl), alicyclics (cyclohexanoyl), and heterocyclics (thiazolyl) are found in various macrocyclic polyketides. Recent studies have shown that modular PKSs have relaxed specificity for their starter units (Kao et al. *Science* (1994), supra). Modular PKSs also exhibit considerable variety with regard to the choice of extender units in each condensation cycle. The degree of β-ketoreduction following a condensation reaction has also been shown to be altered by genetic manipulation (Donadio et al. *Science* (1991), supra; Donadio, S. et al. *Proc Natl Acad Sci USA* (1993) 90:7119–7123). Likewise, the size of the polyketide product can be varied by designing mutants with the appropriate number of modules (Kao, C. M. et al. *J Am Chem Soc* (1994) 116:11612–11613). Lastly, these enzymes are particularly well-known for generating an impressive range of asymmetric centers in their products in a highly controlled manner. Thus, the combinatorial potential within modular PKS pathways based on any naturally occurring modular, such as the erythromycin PKS scaffold, is virtually unlimited.

Methods to Construct Multiple Modular PKS Derived from a Naturally Occurring PKS The derivatives of a naturally occurring PKS can be prepared by manipulation of the relevant genes. A large number of modular PKS gene clusters have been mapped and/or sequenced, including erythromycin and rapamycin, which have been completely mapped and sequenced, and soraphen A, FK506 and oleandomycin which have been partially sequenced, and candicidin, avermectin, and nemadectin which have been mapped and partially sequenced. Additional modular PKS gene clusters are expected to be available as time progresses. These genes can be manipulated using standard techniques to delete or inactivate activity encoding regions, insert regions of genes encoding corresponding activities from the same or different PKS system, or otherwise mutated using standard procedures for obtaining genetic alterations. Of course, portions of, or all of, the desired derivative coding sequences can be synthesized using standard solid phase synthesis methods such as those described by Jaye et al., *J Biol Chem* (1984) 259:6331 and which are available commercially from, for example, Applied Biosystems, Inc.

In order to obtain nucleotide sequences encoding a variety of derivatives of the naturally occurring PKS, and thus a variety of polyketides for construction of a library, a desired number of constructs can be obtained by "mixing and matching" enzymatic activity-encoding portions, and mutations can be introduced into the native host PKS gene cluster or portions thereof Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *BioTechniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc Natt Acad Sci USA* (1982) 79;6409. PCR mutagenesis will also find use for effecting the desired mutations.

Random mutagenesis of selected portions of the nucleotide sequences encoding enzymatic activities can be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals. Chemical mutagens include, for example, sodium bisulfite, nitrous acid, hydroxylamine, agents which damage or remove bases thereby preventing normal base-pairing such as hydrazine or formic acid, analogues of nucleotide precursors such as nitrosoguanidine, 5-bromouracil, 2-arninopurine, of acridine intercalating agents such as proflavine, acriflavine, quinacrine, and the like. Generally, plasmid DNA or DNA fragments are treated with chemicals, transformed into *E. coli* and propagated as a pool or library of mutant plasmids.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication WO 96/40968.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Suitable control sequences include those which function in eucaryotic and procaryotic host cells. Preferred hosts include fungal hosts such as yeast and procaryotic hosts, but single cell cultures of, for example, mammalian cells could also be used. There is no particular advantage, however, in using such systems. Particularly preferred are yeast and procaryotic hosts which use control sequences compatible with Streptomyces spp. Suitable controls sequences for single cell cultures of various types of organisms are well known in the art. Control systems for expression in yeast, including controls which effect secretion are widely available and routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from aromatic (Type II) PKS gene clusters. Examples are act promoters, tcm promoters, spiramycin promoters, and the like. However, other bacterial promoters, such as those derived from genes that encode sugar metabolizing enzymes, such as galactose, lactose (lac) and maltose, are also useful. Additional examples include promoters derived from genes that encode biosynthetic enzymes such as the tryptophan (trp), the β-lactamase (bla) promoters, as well as the bacteriophage lambda PL, and T5 promoters. In addition, synthetic promoters, such as the tac promoter (U.S. Pat. No. 4,551,433), can be used.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for screening cells successfully transformed by the present constructs.

The various PKS nucleotide sequences, or a cocktail of such sequences, can be cloned into one or more recombinant vectors as individual cassettes, with separate control elements, or under the control of, e.g., a single promoter. The PKS subunits or cocktail components can include flanking restriction sites to allow for the easy deletion and insertion of other PKS subunits or cocktail components so that hybrid PKSs can be generated. The design of such unique restriction sites is known to those of skill in the art and can be accomplished using the techniques described above, such as site-directed mutagenesis and PCR.

As described above, particularly useful control sequences are those which themselves, or using suitable regulatory systems, activate expression during transition from growth to stationary phase in the vegetative mycelium. The system contained in the illustrated plasmid pCK7, i.e., the actI/actIII promoter pair and the actII-ORF4, an activator gene, is particularly preferred. Particularly preferred hosts are those which lack their own means for producing polyketides so that a cleaner result is obtained. Illustrative host cells of this type include the modified *S. coelicolor* CH999 culture described in PCT publication WO 96/40968 and similar strains of *S. lividans*.

The expression vectors containing nucleotide sequences encoding a variety of PKS systems for the production of different polyketides are then transformed into the appropriate host cells to construct the library. In one straightforward approach, a mixture of such vectors is transformed into the selected host cells and the resulting cells plated into individual colonies and selected for successful transformants. Each individual colony will then represent a colony with the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products.

The number of members in the library is arbitrarily chosen; however, the degrees of freedom outlined above with respect to the variation of starter, extender units, stereochemistry, oxidation state, and chain length allow quite large libraries to be constructed.

Methods for introducing the recombinant vectors of the present invention into suitable hosts are known to those of skill in the art and typically include the use of $CaCl_2$ or other agents, such as divalent cations, lipofection, DMSO, protoplast transformation and electroporation.

The polyketide producing colonies can be identified and isolated using known techniques and the produced polyketides farther characterized. The polyketides produced by these colonies can be used collectively in a panel to represent a library or may be assessed individually for activity.

The libraries can thus be considered at three levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; and (3) the polyketides produced. Of course, combination libraries can also be constructed wherein members of a library derived, for example, from the erythromycin PKS cluster can be considered as a part of the same library as those derived from, for example, the rapamycin PKS cluster.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competitleon assay. Means to screen such libraries for binding are well known in the art.

Alternatively, individual polyketide members of the library can be tested against a desired target. In this event, screens wherein the biological response of the target is measured can more readily be included.

EXAMPLES

The following examples are intended to illustrate, but not to limit the invention.

Materials and Methods General Techniques

Bacterial strains, plasmids, and culture conditions. *S. coelicolor* CH999 described in PCT publication WO 95/08548, published Mar. 30, 1995 was used as an expression host. DNA manipulations were performed in *Escherichia coli* MC1061. Plasmids were passaged through *E. coli* ET12567 (dam dcm hsdS $Cm^r$) (MacNeil, D. J. *J Bacteriol* (1988) 170:5607) to generate unmethylated DNA prior to transformation of *S. coelicolor*. *E. coil* strains were grown under standard conditions. *S. coelicolor* strains were grown on R2YE agar plates (Hopwood, D. A. et al. *Genetic manipulation of Streptomyces. A laboratory manual*. The John Innes Foundation: Norwich, 1985). pRM5, also described in WO 95/08548, includes a colEI replicon, an appropriately truncated SCP2* Streptomyces replicon, two act-promoters to allow for bidirectional cloning, the gene encoding the actII-ORF4 activator which induces transcription from act promoters during the transition from growth phase to stationary phase, and appropriate marker genes. Engineered restriction sites facilitate the combinatorial construction of PKS gene clusters starting from cassettes encoding individual domains of naturally occurring PKSs.

When pRM5 is used for expression of PKS, (i) all relevant biosynthetic genes are plasmid-borne and therefore amenable to facile manipulation and mutagenesis in *E. coli,* (ii) the entire library of PKS gene clusters can be expressed in the same bacterial host which is genetically and physiologically well-characterized and presumably contains most, if not all, ancillary activities required for in vivo production of polyketides, (iii) polyketides are produced in a secondary metabolite-like manner, thereby alleviating the toxic effects of synthesizing potentially bioactive compounds in vivo, and (iv) molecules thus produced undergo fewer side reactions than if the same pathways were expressed in wild-type organisms or blocked mutants.

Manipulation of DNA and organisms. Polymerase chain reaction (PCR) was performed using Taq polymerase (Perkin Elmer Cetus) under conditions recommended by the enzyme manufacturer. Standard in vitro techniques were used for DNA manipulations (Sambrook, et al. *Molecular Cloning: A Laboratory Manual* (Current Edition)). *E. coli* was transformed with a Bio-Rad *E. Coli* Pulsing apparatus using protocols provided by Bio-Rad. *S. coelicolor* was transformed by standard procedures (Hopwood, D. A. et al. *Genetic manipulation of Streptomyces. A laboratory manual*. The John Innes Foundation: Norwich, 1985) and transformants were selected using 2 ml of a 500 $\mu$g/ml thiostrepton overlay.

Production and purification of polyketides. For initial screening, all strains were grown at 30° C. as confluent lawns on 150 mm Petri plates containing 50 ml of R2YE agar supplemented with 50 $\mu$g/ml thiostrepton poured over a 125 mm disc of Whatman 52 filter paper. After 2–3 days of growth, the agar disc was lifted from the dish and placed atop a layer of 6 mm glass beads mixed with 60 ml of liquid R2YE medium and 3 g of Amberlite XAD-16 absorption resin in a 150 mm Petri dish. Growth was continued for an additional 6 days at 30° C. The agar disc was removed, and the XAD-16 resin was collected by vacuum filtration. After washing with water, the resin was shaken with 15 ml of ethanol for 30 min. The ethanol extract was decanted from the resin, and the extraction was repeated twice more. The combined ethanol extracts were then evaporated to dryness under reduced pressure. The residue was dissolved in ethyl acetate, washed once with saturated aqueous $NaHCO_3$, then analyzed by HPLC (water-acetonitrile-acetic acid gradient, C18-reversed phase) with mass spectrometric detection. For purification, extracts were separated on silica gel columns by silica gel preparative thin-layer chromatography using ethyl acetate-hexane mixtures as eluents.

Preparation A

Construction of the Complete Erythromycin PKS Gene Cluster Recovery of the Ervthomycin PKS Genes Although various portions of the erythromycin PKS gene cluster can be manipulated separately at any stage of the process of preparing libraries, it may be desirable to have a convenient source of the entire gene cluster in one place. Thus, the entire erythromycin PKS gene cluster can be recovered on a single plasmid if desired. This is illustrated below utilizing derivatives of the plasdid pMAK705

(Hamilton et al. *J Bacteriol* (1989) 171:4617) to permit in vivo recombination between a temperature-sensitive donor plasmid, which is capable of replication at a first, permissive temperature and incapable of replication at a second, non-permissive temperature, and recipient plasmid. The eryA genes thus cloned gave pCK7, a derivative of pRM5 (McDaniel et al. *Science* (1993) 262:1546). A control plasmid, pCK7f, was constructed to carry a frameshift mutation in eryAI. pCK7 and pCK7f possess a ColEI replicon for genetic manipulation in *E. coli* as well as a truncated SCP2* (low copy number) Streptomyces replicon.

These plasmids also contain the divergent actI/actIII promoter pair and actII-ORF4, an activator gene, which is required for transcription from these promoters and activates expression during the transition from growth to stationary phase in the vegetative mycelium. High-level expression of PKS genes occurs at the onset of the stationary phase of mycelial growth. The recombinant strains therefore produce the encoded polyketides as secondary metabolites.

Figure 3:
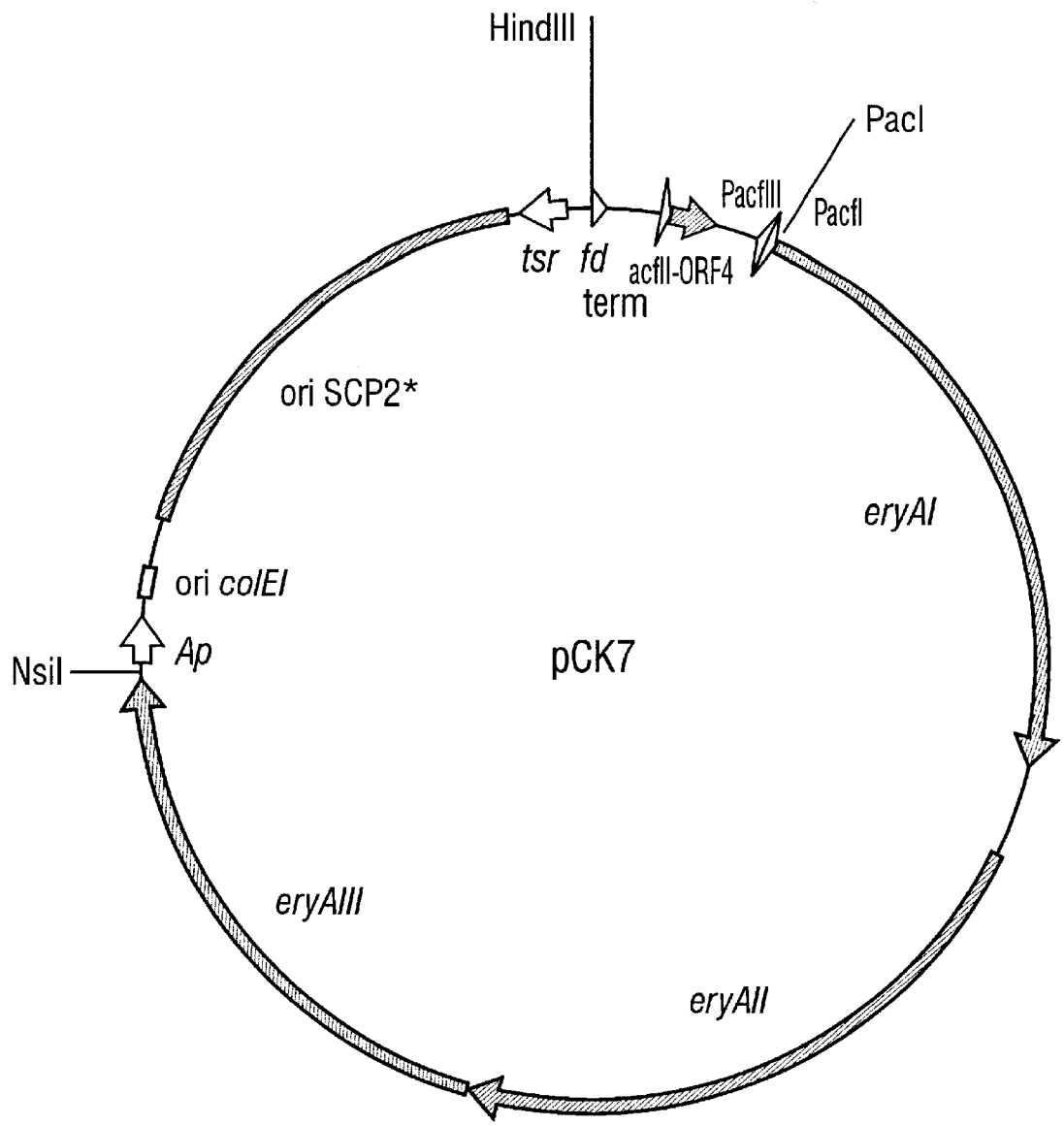
FIG. 3 shows a diagram of a vector containing the entire erythromycin gene cluster.
Figure 4:
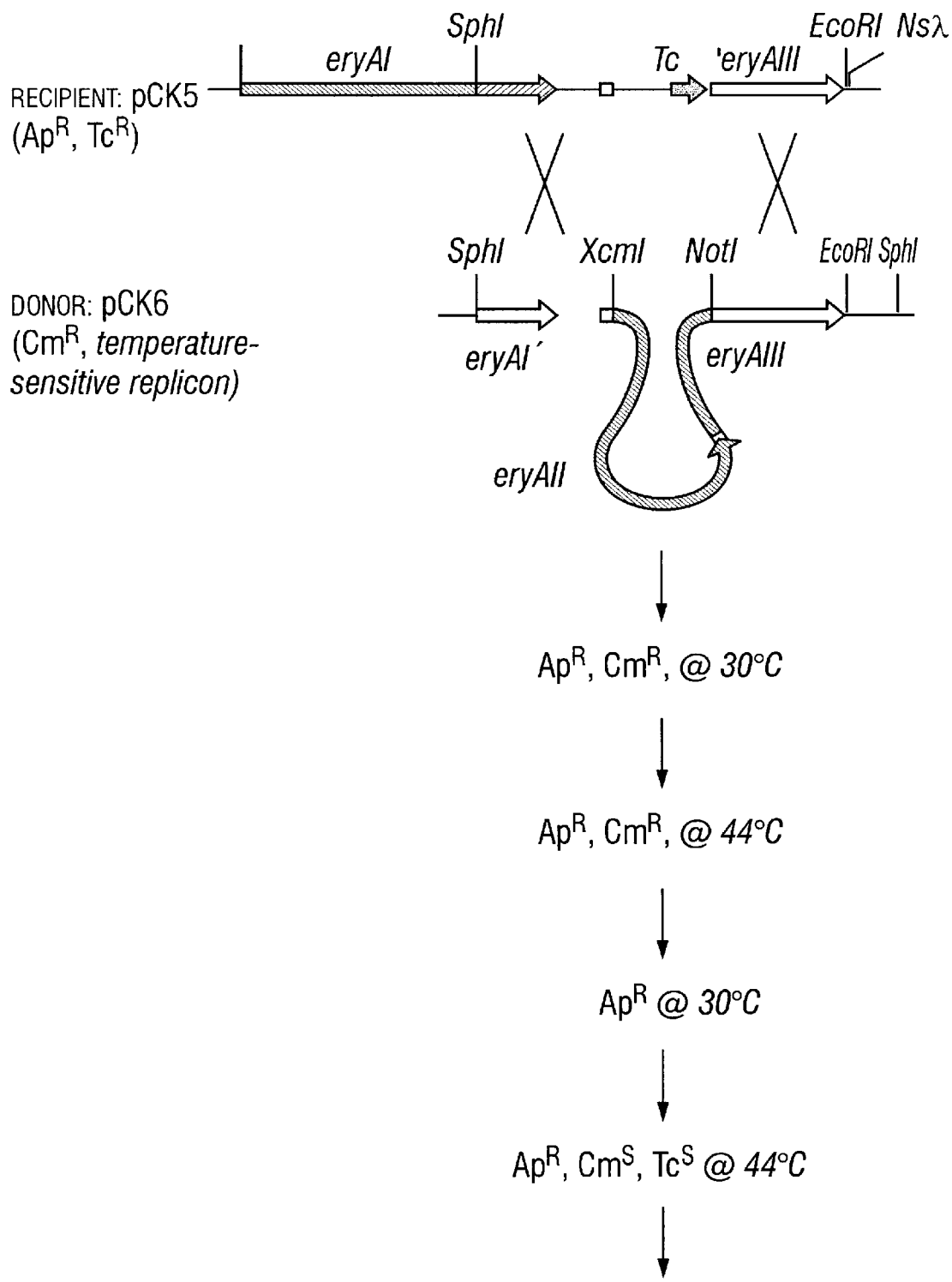
FIG. 4 shows a method for the construction of the vector of FIG. 3.
Figure 5A:
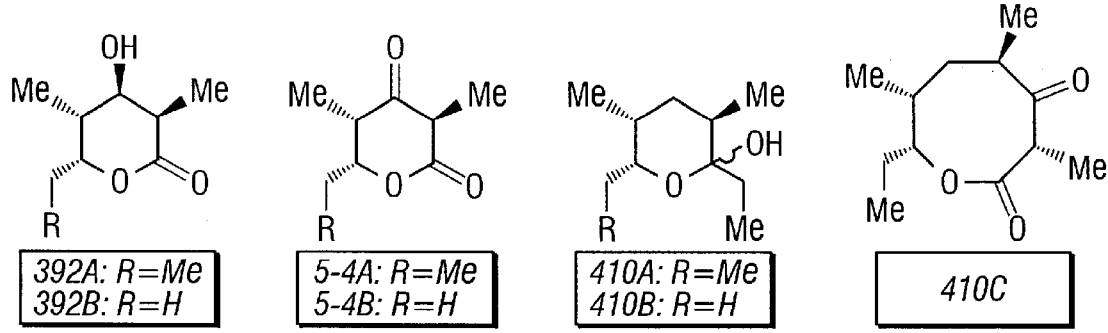
FIG. 5 shows the structures of several polyketides produced by manipulating the erythromycin PKS gene cluster.
Figure 5A:
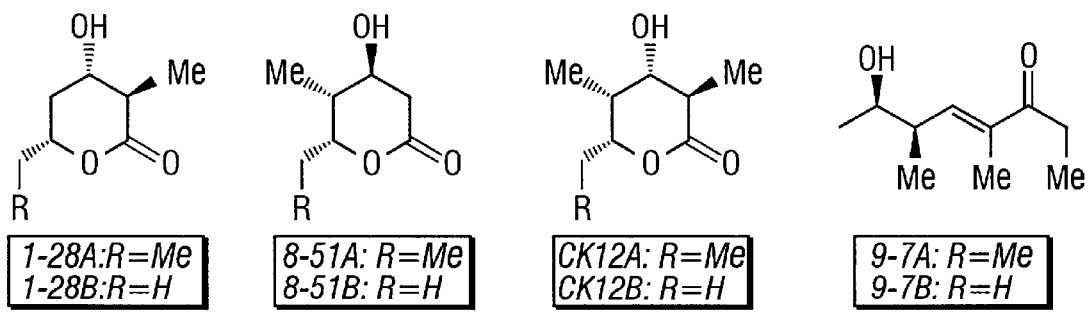
Figure 5A:
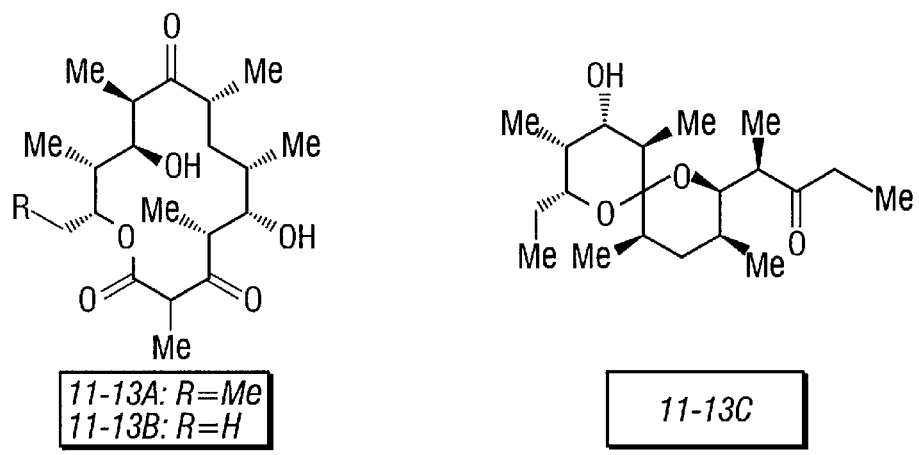
Figure 5B:
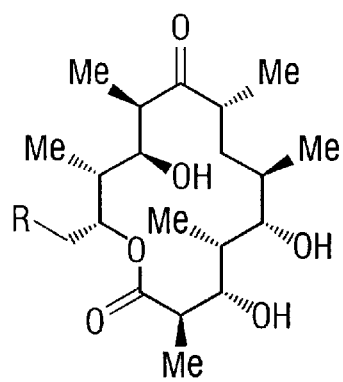
Figure 5B:
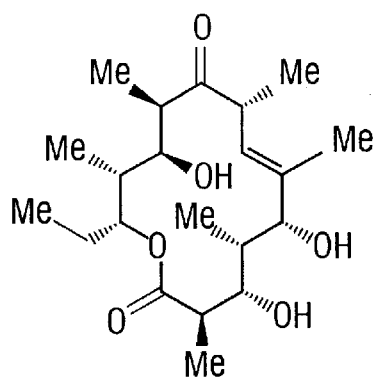
Figure 5B:
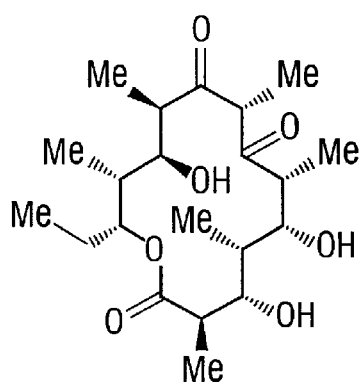
Figure 5B:
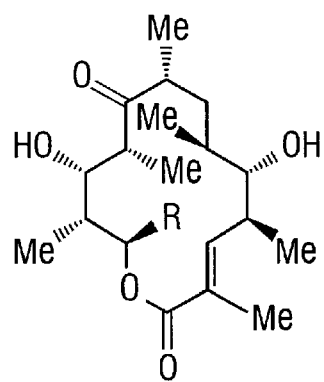
Figure 5B:
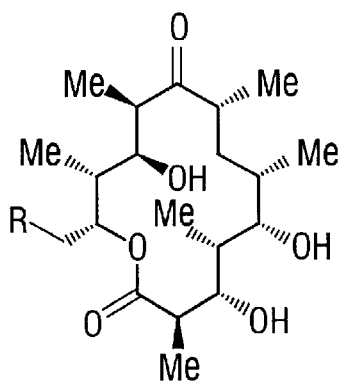

In more detail, pCK7 (FIG. 3), a shuttle plasmid containing the complete eryA genes, which were originally cloned from pS1 (Tuan et al. *Gene* (1990) 90:21), was constructed as follows. The modular DEBS PKS genes were transferred incrementally from a temperature-sensitive "donor" plasmid, i.e., a plasmid capable of replication at a first, permissive temperature and incapable of replication at a second, non-permissive temperature, to a "recipient" shuttle vector via a double recombination event) as depicted in FIG. 4. A 25.6 kb SphI fragment from pS1 was inserted into the SphI site of pMAK705 (Hamilton et al. *J Bacteriol* (1989) 171:4617) to give pCK6 ($Cm^R$), a donor plasmid containing eryAII, eryAIII, and the 3' end of eryAI. Replication of this temperature-sensitive pSC101 derivative occurs at 30° C. but is arrested at 44° C. The recipient plasmid, pCK5 ($Ap^R$, $Tc^R$), includes a 12.2 kb eryA fragment from the eryAI start codon (Caffrey et al. *FEBS Lett* (1992) 304:225) to the XcmI site near the beginning of eryAII, a 1.4 kb EcoRI-BsmI pBR322 fragment encoding the tetracycline resistance gene (Tc), and a 4.0 kb NotI-EcoRI fragment from the end of eryAIII. PacI, NdeI, and ribosome binding sites were engineered at the eryAI start codon in pCK5. pCK5 is a derivative of pRM5 (described above). The 5' and 3' regions of homology are 4.1 kb and 4.0 kb, respectively. MC1061 *E. coli* was transformed with pCK5 and pCK6 and subjected to carbenicillin and chloramphenicol selection at 30° C. Colonies harboring both plasmids ($Ap^R$, $Cm^R$) were then restreaked at 44° C. on carbenicillin and chloramphenicol plates. Only cointegrates formed by a single recombination event between the two plasmids were viable. Surviving colonies were propagated at 30° C. under carbenicillin selection, forcing the resolution of the cointegrates via a second recombination event. To enrich for pCK7 recombinants, colonies were restreaked again on carbenicillin plates at 44° C. Approximately 20% of the resulting colonies displayed the desired phenotype ($Ap^R$, $Tc^S$, $Cm^S$). The final pCK7 candidates were thoroughly checked via restriction mapping. A control plasmid, pCK7f, which contains a frameshift error in eryAI, was constructed in a similar manner. pCK7 and pCK7f were transformed into *E. coli* ET12567 (MacNeil *J Bacteriol* (1988) 170:5607) to generate unmethylated plasmid DNA and subsequently moved into *Streptomyces coelicolor* CH999.

Upon growth of CH999/pCK7 on R2YE medium, the organism produced abundant quantities of two polyketides. The addition of propionate (300 mg/L) to the growth medium resulted in approximately a two-fold increase in yield of polyketide product. Proton and $^{13}C$ NMR spectroscopy, in conjunction with propionic-1-$^{13}C$ acid feeding experiments, confirmed the major product as 6dEB (>40 mg/L). The minor product was identified as 8,8a-deoxyoleandolide (>10 mg/L), which apparently originates from an acetate starter unit instead of propionate in the 6dEB biosynthetic pathway. $^{13}C_2$ sodium acetate feeding experiments confirmed the incorporation of acetate into the minor product. Three high molecular weight proteins (>200 kDa), presumably DEBS1, DEBS2, and DEBS3 (Caffrey et al. *FEBS Lett* (1992) 304:225), were also observed in crude extracts of CH999/pCK7 via SDS-polyacrylamide gel electrophoresis. No polyketide products were observed from CH999/pCK7f. The inventors hereby acknowledge support provided by the American Cancer Society (IRG-32–34).

Example 1

Preparation of Cassettes from the Rapamycin PKS

A cosmid library of genomic DNA from *Streptomyces hygroscopicus* ATCC 29253 was used to prepare DNA cassettes prepared from the rapamycin PKS gene cluster to be used as replacements into the enzymatic activity regions of the erythromycin gene cluster. Cassettes were prepared by PCR amplification from appropriate cosmids or subclones using the primer pairs listed in Table 1. (The rapDH/ER/KR1 cassette sequence was amplified in two halves, then joined at the engineered xhoI site.)

TABLE 1

Primer pairs used for PCR amplification of rapamycin PKS cassettes.
All primers are listed from 5' to 3'.

| Module | Primer Sequence |
|---|---|
| rapAT2 (SEQ ID NO:1 and SEQ ID NO:2) | forward: TTTAGATCTGTGTTCGTCTTCCCGGGT<br>reverse: TTTCTGCAGCCAGTACCGCTGGTGCTGGAAGGCGTA |
| rapKR2 (SEQ ID NO:3 and SEQ ID NO:4) | forward: TTTCTGCAGGAGGGCACGGACCGGGCGACTGCGGGT<br>reverse: TTTTCTAGAACCGGCGGCAGCGGCCCGCCGAGCAAT |
| rapDH/KR4 (SEQ ID NO:5 and SEQ ID NO:6) | forward: TTCTGCAGAGCGTGGACCGGGCGGCT<br>reverse: TTTTCTAGAGTCACCGGTAGAGGCGGCCCT |
| rapDH/ER/KR1 (left half)(SEQ ID NO:7 and SEQ ID NO:8) | forward: TTTCTGCAGGGCGTGGACCGGGCGGCTGCC<br>reverse: TTTCTCGAGCACCACGCCCGCAGCCTCACC |

TABLE 1-continued

Primer pairs used for PCR amplification of rapamycin PKS cassettes.
All primers are listed from 5' to 3'.

| Module | Primer Sequence |
| --- | --- |
| rapDH/ER/KR1 (right half) | forward: TTTCTCGAGGTCGGTCCGGAGGTCCAGGAT<br>reverse: TTTTCTAGAATCACCGGTAGAAGCAGCCCG |

Example 2

Replacement of DEBS Modules By Rapamycin PKS Cassettes a) Replacement of DEBS DH/ER/KR4. A portion of the erythromycin gene of module 4 (eryDH/ER/KR4) was replaced either with the corresponding rapamycin activities of the first rapamycin module (rapDR/ER/KR1) or of module 4 of rapamycin (rapDH/KR4). The replacement utilized the technique of Kao et al. *Science* (1994) 265;509–512. A donor plasmid was prepared by first amplifing 1 kbp regions flanking the DH/ER/KR4 of DEBS to contain a PstI site at the 3' end of the left flank and an XbaI site at the 5' end of the right flank. The fragments were ligated into a temperature-sensitive donor plasmid, in a manner analogous to that set forth for KR6 in paragraph b) of this example, and the rapamycin cassettes prepared as described in Example 1 were inserted into the PstI/XbaI sites. The recipient plasmid was pCK7 described in Preparation A. The in vivo recombination technique resulted in the expression plasmid pKOS011–19 (eryDH/ER/KR4→rapDH/ER/KR1) and pKOS011–21 (eryDH/ER/KR4 →rapDH/KR4). The junctions at which the PgtI and XbaI sites were introduced into DEBS in both vectors are as follows (SEQ ID NO:11 and SEQ ID NO:12):

GAGCCCCAGCGGTACTGGCTGCAG rap cassette TCTAGAGCGGTGCAGGCGGCCCCG

The resulting expression vectors were transformed into *S. coelicolor* CH999 and successful transformants grown as described above. The transformant containing the rapDH/ER/KR1 cassette produced the polyketide shown in FIG. 5 as 11–19a; the transformant containing the plasmid with rapDH/KR4 cassette produced the polyketide shown in FIG. 5 as 11–12a. As shown, these polyketides differ from 6-deoxyerythronolide B by virtue of a 6,7 alkene in the case of 11–21a and by the C6-methyl stereochemistry in the case of 11–19a.

b) Replacement of DEBS KR6. In a manner analogous to that set forth in paragraph a), plasmid pKOS011–25, wherein eryKR6 was replaced by rapDH/KR4, was prepared by substituting regions flanking the KR6 domain of DEBS in construction of the donor plasmid.

Approximately 1 kb regions flanking the eryKR6 domain were PCR amplified with the following primers (SEQ ID NO:13 through SEQ ID NO:16):

| left flank | forward | 5'-TTTGGATCCGTTTTCGTCTTCCCAGGTCAG |
| | reverse | 5'-TTTCTGCAGCCAGTACCGCTGGGGCTCGAA |
| right flank | forward | 5'-TTTTCTAGAGCGGTGCAGGCGGCCCCGGCG |
| | reverse | 5'-AAAATGCATCTATGAATTCCCTCCGCCCA |

These fragments were then cloned into a pMAK705 derivative in which the multiple cloning site region was modified to accommodate the restriction sites of the fragments (i.e., BamBI/PstI for the left flank and XbaI/NsiI for the right flank). Cassettes were then inserted into the PstI/XbaI sites of the above plasmid to generate donor plasmids for the in vivo recombination protocol. The resulting PstI and XbaI junctions engineered into DEB S are as follows (SEQ ID NO:17 and SEQ ID NO:18):

GAACACCAGCGCTTCTGGCTGCAG rap cassette TCTAGAGACCGGCTCGCCGGTCGG

Transformants of *S. coelicolor* CH999 resulted in the production of the polyketide shown in FIG. 5 as 11–25 a,b. Regions flanking the KR6 domain of DEBS were used to construct the donor plasmids.

c) Replacement of DEBS KR2. The eryKR2 enzymatic activity was replaced in a series of vectors using in vitro insertion into the PstI/XbaI sites of pKAO263. pKAO263 is a derivative of pCK13 described in Kao, C. M. *J Am Chem Soc* (1996) 118:9184–9185. It was prepared by introducing the PstI and XbaI restriction sites positioned identically to those in the analogous 2-module DEBS system described by Bedford, D. et al. *Chem Biol* (1996) 3:827–831. Three expression plasmids were prepared: pKO2009-7 (eryKR2→rapDH/KR4); pKAO392 (eryKR2→rapKR2); and pKAO410 (eryKR2→rapDH/ER/KR1). These lasmids, when transformed into *S. coelicolor* CH999, resulted in the production of polyketides with the structures 9–7 a,b, 392 a,b; and 410 a,b,c in FIG. 5, respectively. An additional vector, pKAO400 (eryKR2→rapKR4) produced the same results as pKAO392.

d) Replacement of DEBS AT2. The DEBS AT activity from module 2 was excised after inserting restriction sites BamHI and PstI flanking the AT module 2 domain into pCK12 (Kao et al. *J Am Chem Soc* (1995) 112:9105–9106). After digestion with BamHI/PstI, the BglII/PstI fragment containing rapAT2 was inserted. The resulting engineered DEBS/rapAT2 junction is as follows (BamHI/BglII ligation—GGATCT; PstI-CTGCAG): (SEQ ID NO:22 and SEQ ID NO:23)

AGTGCCTCCGACGGTGGATCT rapAT2 CTGCAGC-CGGACCGCACCACCCCT

*S. coelicolor* CH999 transformed with the resulting plasmid, pKOS008–51, produced the polyketides 8–51 a,b shown in FIG. 5.

Example 3

Excision of DEBS Reductive Cycle Domains

A duplex oligonucleotide linker (ΔRdx) was designed to allow complete excision of reductive cycle domains. Two synthetic oligonucleotides (SEQ ID NO:24 and SEQ ID NO:2:

5'-GCCGGACCGCACCACCCCTCGTGACGGAGA ACCGGAGACGGAGAGCT-3'
3'-ACGTCGGCCTGGCGTGGTGGGGAGCACTGC CTCTTGGCCTCTGCCTCTCGAGATC-5' were designed to generate PstI- and XbaI-compatible ends upon hybridization. This duplex linker was ligated into the PstI- and XbaI-sites of the recombination donor plasmid contaiming the appropriate left- and right-flanking regions of the reductive domain to be excised. The in vivo recombination technique of Example 2, paragraph a) was then used. The donor plasmid contained the duplex linker ΔRdx having a PstI and XbaI compatible end ligated into the PstI and XbaI sites of the plasmid modified to contain the left and right flanking regions of the reductive domain to be excised. The donor plasmids were recombined with recipient plasmid pCK7 to generate pKOS011–13 (eryKR6→ΔRdx) and with recipient plasrnid pCK13 to obtain pKOS005–4 (eryKR2→ΔRdx). These plasmids generated, when transformed into *S. coelicolor* CH999, the polyketides 11–13 a,b,c and 5–4 a,b in FIG. 5, respectively.

Example 4

Summary of DEBS Constructs

Using the foregoing techniques, the DEBS constructs shown in Table 2 were constructed.

TABLE 2

Representative DEBS Constructs.

| plasmid | modules | genotype | products |
| --- | --- | --- | --- |
| pKOS005-4 | 3 | eryKR2 → ΔRdx | 5-4a,b |
| pKOS008-51 | 2 | eryAT2 → rapAT2 | 8-51a,b |
| pKOS009-7 | 3 | eryKR2 → rapDH/KR4 | 9-7a,b |
| pKOS011-13 | 6 | eryKR6 → ΔRdx | 11-13a,b,c |
| pKOS011-19 | 6 | eryDH/ER/KR4 → rapDH/ER/KR1 | 11-19a,b |
| pKOS011-21 | 6 | eryDH/ER/KR4 → rapDH/KR4 | 11-21a |
| pKOS011-22 | 6 | eryDH/ER/KR4 → ΔRdx | 11-22a |
| pKOS011-25 | 6 | eryKR6 → rapDH/KR4 | 11-25a,b |
| pKOS011-28 | 2 | eryAT1 → rapAT2 | 11-28a,b |
| pKOS014-9 | 2 | eryAT2 → rapAT4 | CK12a,b |
| pKAO392 | 3 | eryKR2 → rapKR2 | 392a,b |
| pKAO404 | 3 | eryKR2 → rapKR4 | 392a,b |
| pKAO410 | 3 | eryKR2 → rapDH/ER/KR1 | 410a,b,c |

Example 5

Manipulation of Macrolide Ring Size by Directed Mutagenesis of DEBS

Figure 6A:
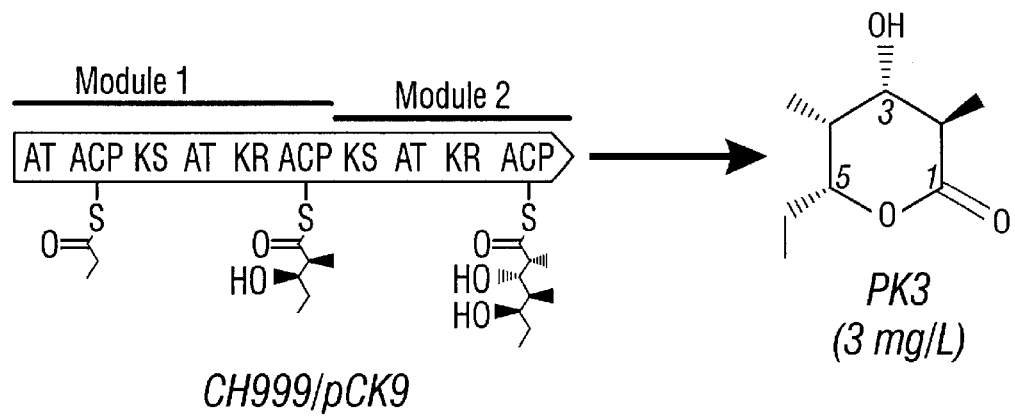
FIGS. 6a and 6b show the construction of derivative PKS gene clusters from the vector of FIG. 3.
Figure 6B:
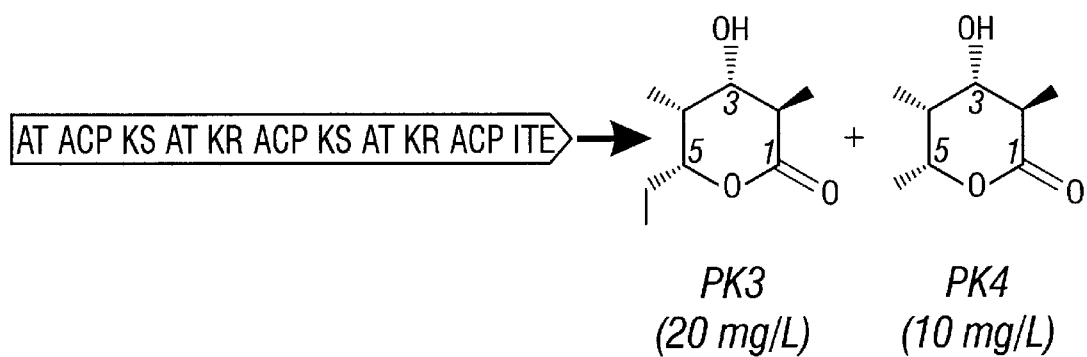
Figure 6C:
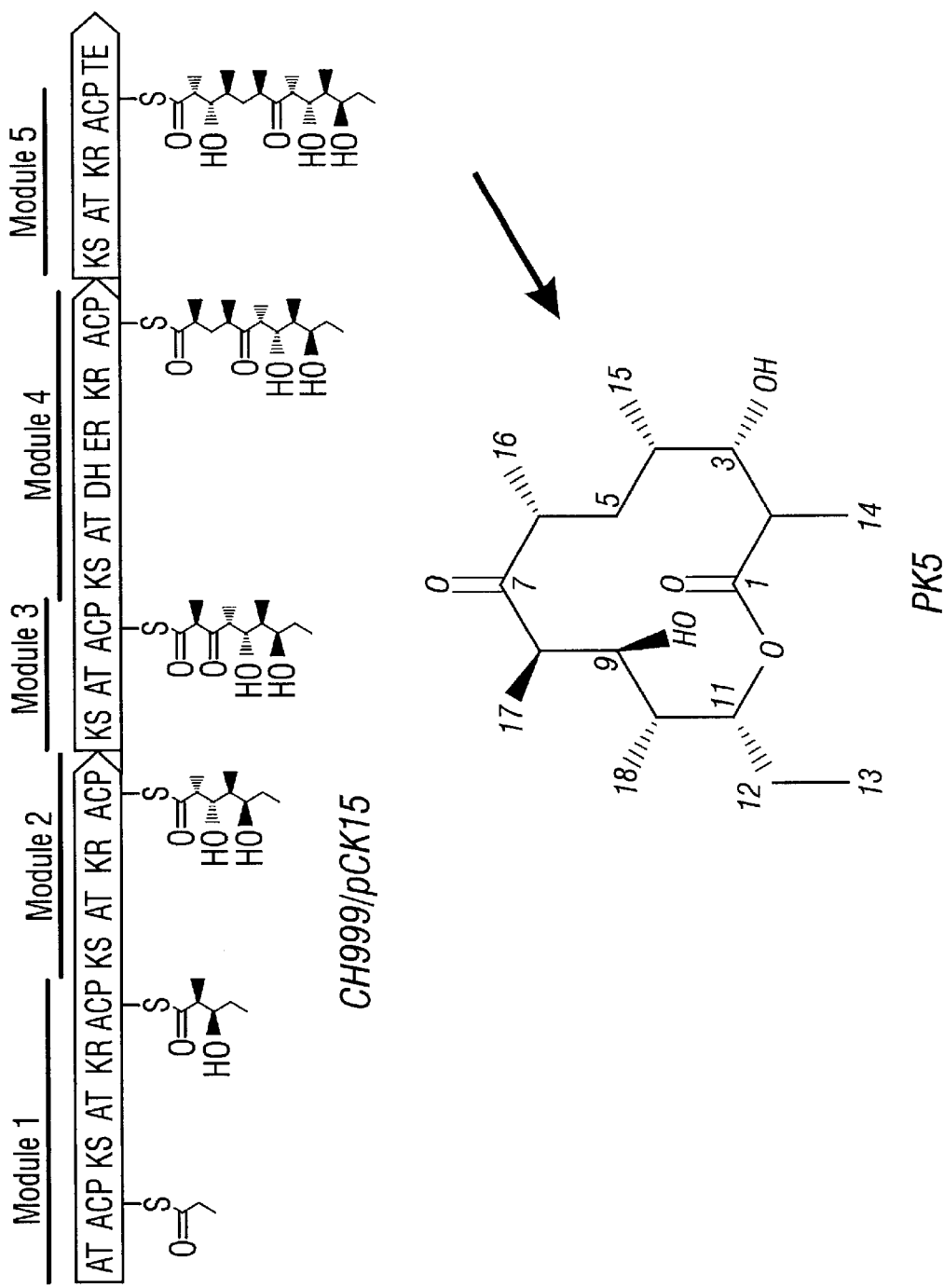
FIG. 6c show the construction of 1+2+3+4+5+TE PKS and the polyketides product.

Using the expression system of Kao, C. M. et al. *Science* (1994) 265:509–512, the expresgion of DEBS1 alone (1+2), in the absence of DEBS2 and DEBS3 (in plasmid pCK9), resulted in the production of (2R,3S,4S,5R)-2,4-dimethyl-3,5-dihydroxy-n-heptanoic acid L-lactone ("the heptanoic acid L-lactone" (PK3) (see FIG. 6)) (1–3 mg/L), the expected triketide product of the first two modules (Kao, C. M. et al. *J Am Chem Soc* (1994) 116:11612–11613). Thus, a thioesterase is not essential for release of a triketide from the enzyme complex.

Two additional deletion mutant PKS were constructed. The first contained DEBS1 fused to the TE, and the second PKS included the first five DEBS modules fused to the TE. Plasmids pCK12 and pCK15 respectively contained the genes encoding the bimodular ("1+2+TE") and pentamodular ("1+2+3+4+5+TE") PKSs.

The 1+2+TE PKS in pCK12 contained a fusion of the carboxy-terminal end of the acyl carrier protein of module 2 (ACP-2) to the carboxy-terminal end of the acyl carrier protein of module 6 (ACP-6). Thus ACP-2 is essentially intact and is followed by the amino acid sequence naturally found between ACP-6 and the TE. Plasmid pCK12 contained eryA DNA originating from pS1 (Tuan, J. S. et al. *Gene* (1990) 90:21). pCK12 is identical to pCK7 (Kao et al. *Science* (1994), supra) except for a deletion between the carboxy-terminal ends of ACP-2 and ACP-6. The fusion occurs between residues L3455 of DEBS1 and Q2891 of DEBS3. An SpeI site is present between these two residues so that the DNA sequence at the fusion is CTCACTAGT-CAG (SEQ ID NO:26).

The 1+2+3+4+5+TE PKS in pCK15 contained a fusion 76 amino acids downstream of the β-ketoreductase of module 5 (KR-5) and five amino acids upstream of ACP-6. Thus, the fusion occurs towards the carboxy-terminal end of the non-conserved region between KR-5 and ACP-5, and the recombinant module 5 was essentially a hybrid between the wild type modules 5 and 6. Plasmid pCK15 contained eryA DNA originating from pS1 (Tuan et al. *Gene* (1990), supra). pCK15is a derivative of pCK7 (Kao et al. *Science* (1994), supra) and was constructed using the in vivo recombination strategy described earlier (Kao et al. *Science* (1994), supra). pCK15 is identical to pCK7 with the exception of a deletion between KR-5 and ACP-6, which occurs between residues G1372 and A2802 of DEBS3, and the insertion of a blunted a SalI fragment containing a kanamycin resistance gene (Oka A. et al. *J Mol Biol* (1981) 147:217) into the blunted HindIII site of pCK7. An arginine residue is present between G1372 and A2802 so that the DNA sequence at the fusion is GGCCGCGCC (SEQ ID NO:27).

Plasmids pCK12 and pCK15 were introduced into *S. coelicolor* CH999 and polyketide products were purified from the transformed strains according to methods previously described (Kao et al. *Science* (1994), supra).

The products obtained from various transformants: CH999/pCK12 and CH999/pCK15 as well as CH999/pCK9 described above, are shown in FIG. 6.

CH999/pCK12 produced the heptanoic acid L-lactone (PK3) (20 mg/L) as determined by $^1$H and $^{13}$C NMR spectroscopy. This triketide product is identical to that produced by CH999/pCK9, which expresses the unmodified DEBS 1 protein alone described above. However, CH999/pCK12 produced PK3 in significantly greater quantities than did CH999/pCK9 (>10 mg/L vs.~1 mg/L), indicating the ability of the TE to catalyze thiolysis of a triketide chain attached to the ACP domain of module 2. CH999/pCK12 also produced significant quantities of PK4, a novel analog of PK3, (10 mg/L), that resulted from the incorporation of an acetate start unit instead of propionate. This is reminiscent of the ability of CH999/pCK7, which expresses the intact PKS, to produce 8,8a-deoxyoleandolide (PK1) in addition to 6dEB (PK2) described above.

Since PK4 was not detected in CH999/pCK9, its facile isolation from CH999/pCK12 provides additional evidence for the increased turnover rate of DEBS1 due to the presence of the TE. In other words, the TE can effectively recognize an intermediate bound to a "foreign" module that is four acyl units shorter than its natural substrate, 6dEB (PK2). However, since the triketide products can probably cyclize spontaneously into PK3 and PK4 under typical fermentation conditions (pH 7), it is not possible to discriminate between a biosynthetic model involving enzyme-catalyzed lactonization and one involving enzyme-catalyzed hydrolysis followed by spontaneous lactonization. Thus, the ability of the 1+2+TE PKS to recognize the C-5 hydroxyl of a triketide as an incoming nucleophile is unclear.

CH999/pCK15, produced abundant quantities of (8R,9S)-8,9-dihydro-8-methyl-9-hydroxy-10-deoxymethonolide ("the 10-deoxymethonolide)(PK5) (10 mg/L), demonstrating that the pentamodular PKS is active. PK5 was characterized using $^1$H and $^{13}$C NMR spectroscopy of natural abundance and $^{13}$C-enriched material, homonuclear correlation spectroscopy (COSY), heteronuclear correlation spectroscopy (HETCOR), mass spectrometry, and molecular modeling. PK5 is an analog of 10-deoxymethonolide (Lambalot, R. H. et al. *J Antibiotics* (1992) 45:1981–1982), the aglycone of the macrolide antibiotic methymycin. The production of PK5 by a pentamodular enzyme demonstrates that active site domains in modules 5 and 6 in DEBS can be joined without loss of activity. Thus, it appears that individual modules as well as active sites are independent entities which do not depend on association with neighboring modules to be functional. The 12-membered lactone ring, formed by esterification of the terminal carboxyl with the C-11 hydroxyl of the hexaketide product, indicated the ability of the 1+2+3+4+5+TE PKS, and possibly the TE itself, to catalyze lactonization of a polyketide chain one acyl unit shorter than the natural product of DEBS, 6dEB. Indeed, the formation of the PK5 may mimic the biosynthesis of the closely related 12-membered hexaketide macrolide, methymycin, which frequently occurs with the homologous 14-membered heptaketide macrolides, picromycin and/or narbomycin (Cane, D. E. et al. *J Am Chem Soc* (1993) 115:522–566). The erythromycin PKS scaffold can thus be used to generate a wide range of macrolactones with shorter as well as longer chain lengths.

The construction of the 1+2+3+4+5+TE PKS resulted in the biosynthesis of a previously uncharacterized 12-membered macrolactone that closely resembles, but is distinct from, the aglycone of a biologically active macrolide. The apparent structural and functional independence of active site domains and modules as well as relaxed lactonization specificity suggest the existence of many degrees of freedom for manipulating these enzymes to produce new modular PKSs.

---

What is claimed is:

1. A method to prepare a nucleic acid encoding a functional, complete, modified erytromycin PKS, said method comprising: replacing, in a nucleic acid encoding the natural, complete erythromycin PKS, a nucleotide sequence encoding an acyl transferase (AT) catalytic region that employs methylmalonyl as an extender unit with a nucleotide sequence encoding an AT catalytic region that employs malonyl as an extender unit, wherein said AT catalytic region that employs a malonyl extender unit is derived from a rapamycin PKS.

2. A nucleic acid encoding a modified erythromycin PKS prepared by the method of claim 1.

3. A method to prepare a cell containing an expression system for a modified erythromycin PKS, which method comprises introducing into a cell an expression system that comprises the nucleic acid of claim 2 encoding said modified PKS operably linked to a control sequence for expression.

4. A cell that produces a modified erythromycin PKS which is prepared by the met hod of claim 3.

5. A method to prepare a modified erythromycin PKS, which method comprises culturing the cell of claim 4 under conditions such that said modified erythromycin PKS is produced.

6. The method of claim 1, wherein said replacing is without substantial alteration of a nucleotide sequence encoding scaffolding regions in said module in which said AT catalytic region that employs methylmalonyl as an extender unit is replaced.

7. A method to prepare a nucleic acid encoding a functional modified complete erythromycin PKS, said method comprising:

replacing, in a nucleic acid encoding the naturally occurring erythromycin PKS, a nucleotide sequence encoding a first complete beta-keto modifying (BKM) catalytic region containing (1) a ketoreductase activity (KR) or (2) a KR and a dehydratase activity (DH) or (3) a KR plus DH plus enoyl reductase activity (ER), and scaffolding regions immediately adjacent thereto with a nucleotide sequence encoding a second BKM catalytic region and the scaffolding regions immediately adjacent thereto derived from rapamycin PKS.

8. A nucleic acid encoding a modified erythromycin PKS prepared by the method of claim 7.

9. A method to prepare a cell containing an expression system for a modified erythromycin PKS, which method comprises introducing into a cell an expression system that comprises a nucleic acid of claim 8 encoding said modified PKS operably linked to a control sequence for expression.

10. A cell that produces a modified erythromycin PKS which is prepared by the method of claim 9.

11. A method to prepare a modified erythromycin PKS, which method comprises cultrring the cell of claim 10 under conditions such that said modified erythromycin PKS is produced.

12. A method to prepare a nucleic acid encoding a functional modified complete erythromycin PKS, said method comprising: deleting, in a nucleic acid encoding the natural erythromycin PKS, a nucleotide sequence encoding a complete beta-keto-modifying (BKM) catalytic region and the scaffolding regions inmmediately adjacent thereto.

13. A nucleic acid encoding a modified erythromycin PKS prepared by the method of claim 12.

14. A method to prepare a cell containing an expression system for a modified erythromycin PKS, which method comprises introducing into a cell an expression system that comprises a nucleic acid of claim 13 encoding said modified PKS operably linked to a control sequence for expression.

15. A cell that produces a modified erythromycin PKS prepared by the method of claim 14.

16. A method to prepare a modified erythromycin PKS, which method comprises culturing the cell of claim 15 under conditions such that said modified erythromycin PKS is produced.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (xi) SEQUENCE DESCRIPTION: SEQ ID NO:1:

TTTAGATCTG TGTTCGTCTT CCCGGGT      27

(2) INFORMATION FOR SEQ ID NO:2:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:2:

TTTCTGCAGC CAGTACCGCT GGTGCTGGAA GGCGTA      36

(2) INFORMATION FOR SEQ ID NO:3:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:3:

TTTCTGCAGG AGGGCACGGA CCGGGCGACT GCGGGT      36

(2) INFORMATION FOR SEQ ID NO:4:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:4:

TTTTCTAGAA CCGGCGGCAG CGGCCCGCCG AGCAAT                                    36

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

TTCTGCAGAG CGTGGACCGG GCGGCT                                               26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:6:

TTTTCTAGAG TCACCGGTAG AGGCGGCCCT                                           30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:7:

TTTCTGCAGG GCGTGGACCG GGCGGCTGCC                                           30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

TTTCTCGAGC ACCACGCCCG CAGCCTCACC                                           30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:9:

TTTCTCGAGG TCGGTCCGGA GGTCCAGGAT                                           30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

TTTTCTAGAA TCACCGGTAG AAGCAGCCCG                                        30

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:11:

GAGCCCCAGC GGTACTGGCT GCAG                                              24

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:12:

TCTAGAGCGG TGCAGGCGGC CCCG                                              24

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

TTTGGATCCG TTTTCGTCTT CCCAGGTCAG                                        30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:14:

TTTCTGCAGC CAGTACCGCT GGGGCTCGAA                                        30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

TTTTCTAGAG CGGTGCAGGC GGCCCCGGCG                                        30

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:16:

AAAATGCATC TATGAATTCC CTCCGCCCA                                    29

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:17:

GAACACCAGC GCTTCTGGCT GCAG                                         24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:18:

TCTAGAGACC GGCTCGCCGG TCGG                                         24

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

AGTGCCTCCG ACGGTGGATC T                                            21

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

CTGCAGCCGG ACCGCACCAC CCCT                                         24

(2) INFORMATION FOR SEQ ID NO:21:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:21:

GCCGGACCGC ACCACCCCTC GTGACGGAGA ACCGGAGACG GAGAGCT                47

(2) INFORMATION FOR SEQ ID NO:22:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:22:

```
                                        -continued

CTAGAGCTCT CCGTCTCCGG TTCTCCGTCA CGAGGGGTGG TGCGGTCCGG CTGCA                55

(2) INFORMATION FOR SEQ ID NO:23:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (xi) SEQUENCE DESCRIPTION: SEQ ID NO:23:

CTCACTAGTC AG                                                              12

(2) INFORMATION FOR SEQ ID NO:24:

(i) SEQUENCE CHARACTERISTICS:
         (A) LENGTH: 9 base pairs
         (B) TYPE: nucleic acid
         (C) STRANDEDNESS: single
         (D) TOPOLOGY: linear (xi) SEQUENCE DESCRIPTION: SEQ ID NO:24:

GGCCCGCC                                                                    9
```